(12) United States Patent
Schilling et al.

(10) Patent No.: US 12,015,281 B2
(45) Date of Patent: Jun. 18, 2024

(54) INTEGRITY MONITORING FOR A TRANSCUTANEOUS ENERGY SYSTEM

(71) Applicant: Medtronic, Inc., Minneapolis, MN (US)

(72) Inventors: Eric A. Schilling, Ham Lake, MN (US); David J. Peichel, Minneapolis, MN (US); Jonathan P. Roberts, Coon Rapids, MN (US); Joel Artmann, Elk River, MN (US); Michael Reinert, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 761 days.

(21) Appl. No.: 17/111,590

(22) Filed: Dec. 4, 2020

(65) Prior Publication Data
US 2021/0220639 A1    Jul. 22, 2021

Related U.S. Application Data

(60) Provisional application No. 62/962,334, filed on Jan. 17, 2020.

(51) Int. Cl.
*H02J 50/80* (2016.01)
*A61M 60/875* (2021.01)
(Continued)

(52) U.S. Cl.
CPC ........... *H02J 50/80* (2016.02); *A61M 60/875* (2021.01); *H02J 50/10* (2016.02); *H02J 50/90* (2016.02);
(Continued)

(58) Field of Classification Search
CPC ....................................................... H02J 50/80
(Continued)

(56) References Cited

U.S. PATENT DOCUMENTS 5,350,413 A * 9/1994 Miller ................. A61N 1/3787
336/115
5,995,874 A * 11/1999 Borza ................. A61N 1/3787
607/61
(Continued)

FOREIGN PATENT DOCUMENTS

EP         2667939 B1      4/2013
WO      2019088760 A1      5/2019

OTHER PUBLICATIONS

International Search Report and Written Opinion dated Mar. 19, 2021, for corresponding International Application No. PCT/US2020/065499; International Filing Date: Dec. 17, 2020 consisting of 10-pages.

*Primary Examiner* — Jerry D Robbins
(74) *Attorney, Agent, or Firm* — Shumaker & Sieffert, P.A.

(57) ABSTRACT

According to one or more embodiments, a system is provided. The system includes a power device implantable within a patient for powering an implantable medical device. The power device includes a first coil configured to receive wireless power signals for powering the implantable medical device and processing circuitry configured to determine at least one measurable electrical characteristic in a plurality of electrical pathways in the power device including an electrical pathway to the first coil, and detect reduced performance in receiving wireless power signals based at least in part on the determined at least one measurable electrical characteristic.

18 Claims, 7 Drawing Sheets

(51) Int. Cl.
*H02J 50/10* (2016.01)
*H02J 50/90* (2016.01)

(52) U.S. Cl.
CPC ..... *A61M 2205/50* (2013.01); *A61M 2205/58* (2013.01); *H02J 2310/23* (2020.01)

(58) Field of Classification Search
USPC ........................................................ 320/108
See application file for complete search history.

(56) References Cited

U.S. PATENT DOCUMENTS

| | | | |
|---|---|---|---|
| 6,592,620 B1* | 7/2003 | Lancisi | A61M 60/232 623/3.27 |
| 7,225,032 B2 | 5/2007 | Schmeling et al. | |
| 8,140,168 B2 | 3/2012 | Olson et al. | |
| 8,974,366 B1* | 3/2015 | Radziemski | A61N 1/37217 600/16 |
| 9,855,376 B2 | 1/2018 | Bluvshtein et al. | |
| 2004/0039423 A1 | 2/2004 | Dolgin | |
| 2010/0217352 A1* | 8/2010 | Forsell | A61N 1/3787 607/61 |
| 2010/0217353 A1* | 8/2010 | Forsell | H02J 50/80 607/61 |
| 2010/0222848 A1* | 9/2010 | Forsell | H02J 50/10 607/61 |
| 2014/0070773 A1 | 3/2014 | Cottrill et al. | |
| 2015/0207331 A1 | 7/2015 | Petersen | |
| 2015/0209590 A1 | 7/2015 | Pan et al. | |
| 2017/0201131 A1* | 7/2017 | Vihvelin | H02J 50/80 |
| 2019/0290819 A1 | 9/2019 | Hansen | |

* cited by examiner

INTEGRITY MONITORING FOR A TRANSCUTANEOUS ENERGY SYSTEM

CROSS-REFERENCE TO RELATED APPLICATION

This application claims the benefit of U.S. Application Ser. No. 62/962,334, filed Jan. 17, 2020.

FIELD

The present technology is generally related to wireless power transfer, in particular, to Transcutaneous Energy Transfer Systems (TETS).

BACKGROUND

Powering implantable medical devices is one aspect of helping ensure the proper function of the medical devices after being implanted. One option to power such medical devices is to use percutaneous wires directly attached to these medical devices to provide power; however, such a configuration is susceptible to infection and reduces patient mobility. Transcutaneous energy transfer systems (TETS) are being developed to provide such power to implantable medical devices such as ventricular assist devices where power can be wirelessly transmitted over a range of skin and/or tissue thicknesses.

SUMMARY

The techniques of this disclosure generally relate to Transcutaneous Energy Transfer Systems (TETS) for wireless transfer of power from an external energy transfer coil to an implantable energy transfer coil. When the application of the power transfer is critical to maintain a life-sustaining therapy such as a fully implanted LVAD system, the ability to detect or predict performance and reliability issues may be important to mitigation against safety hazards. One or more embodiments described herein may be used to monitor the performance integrity of an implanted TET system. One or more embodiments provide one or more of the following:

Long term efficiency trending with either automated or report based notification;

Measurable electrical characteristics such as one or more of periodic impedance and/or continuity check of the connection from the implanted device and the exterior device such as a connection between an iController (i.e., power device) to the iTETS (i.e., external device).

According to one aspect of the invention, a system is provided. The system includes a power device implantable within a patient for powering an implantable medical device. The power device includes a first coil configured to receive wireless power signals for powering the implantable medical device. The power device further includes processing circuitry configured to determine at least one measurable electrical characteristic in a plurality of electrical pathways in the power device including an electrical pathway to the first coil, and detect reduced performance in receiving wireless power signals based at least in part on the determined at least one measurable electrical characteristic.

According to one or more embodiment of this aspect, an external device is positioned outside of the patient for providing power to the implantable medical device. The external device includes a second coil for transmitting power signals, and processing circuitry configured to receive an indication of power received by the power device and determine a wireless power transfer efficiency over a predetermined period of time based at least in part on the received indication of the power received by the power device. According to one or more embodiment of this aspect, the wireless power transfer efficiency over the predetermined period of time corresponds to a long term moving average. According to one or more embodiment of this aspect, the long term moving average indicates whether performance is degrading due to at least one non-alignment factor between the first coil and the second coil.

According to one or more embodiment of this aspect, the at least one non-alignment factor includes at least one of increased fat thickness of a person in which the power device is implanted and degradation of at least one material characteristic of the power device. According to one or more embodiment of this aspect, the processing circuitry is further configured to trigger a notification if the long term moving average meets a predefined threshold. According to one or more embodiment of this aspect, the processing circuitry is further configured to receive an indication of the determined at least one measurable electrical characteristic, and determine a long term moving average based at least in part on the determined at least one measurable electrical characteristic.

According to one or more embodiment of this aspect, the plurality of electrical pathways includes a feedthrough cables, connectors and coil windings. According to one or more embodiment of this aspect, the processing circuitry is further configured to trigger a notification if any one of the at least one measurable electrical characteristic is one of below and above a predefined threshold. According to one or more embodiment of this aspect, the power device is positioned one of proximate and within the medical device.

According to another aspect of the disclosure, a method for a system including a power device implantable within a patient for powering an implantable medical device is provided. The power device includes a first coil configured to receive wireless power signals for powering the implantable medical device. At least one measurable electrical characteristic in a plurality of electrical pathways in the power device including an electrical pathway to the first coil is determined. Reduced performance in receiving wireless power signals is detected based at least in part on the determined at least one measurable electrical characteristic.

According to one or more embodiment of this aspect, the system further includes an external device positioned outside of the patient for providing power to the implantable medical device where the external device includes a second coil for transmitting power signals. An indication of power received by the power device is received. A wireless power transfer efficiency over a predetermined period of time is determined based at least in part on the received indication of the power received by the power device.

According to one or more embodiment of this aspect, the wireless power transfer efficiency over the predetermined period of time corresponds to a long term moving average. According to one or more embodiment of this aspect, the long term moving average indicates whether performance is degrading due to at least one non-alignment factor between the first coil and the second coil. According to one or more embodiment of this aspect, the at least one non-alignment factor includes at least one of increased fat thickness of a person in which the power device is implanted and degradation of at least one material characteristic of the power device.

According to one or more embodiment of this aspect, a notification is triggered if the long term moving average meets a predefined threshold. According to one or more embodiment of this aspect, an indication of the determined at least one measurable electrical characteristic is received. A long term moving average is determined based at least in part on the determined at least one measurable electrical characteristic.

According to one or more embodiment of this aspect, the plurality of electrical pathways includes a feedthrough cables, connectors and coil windings. According to one or more embodiment of this aspect, a notification is triggered if any one of the at least one measurable electrical characteristic is one of below and above a predefined threshold. According to one or more embodiment of this aspect, the power device is positioned one of proximate and within the medical device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of device components and processing steps related to TETS for wireless transfer of power from an external energy transfer coil to an implantable energy transfer coil. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

In some embodiments described herein, the term "coupled," "connected," and the like, may be used herein to indicate a connection, although not necessarily directly, and may include wired and/or wireless connections.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
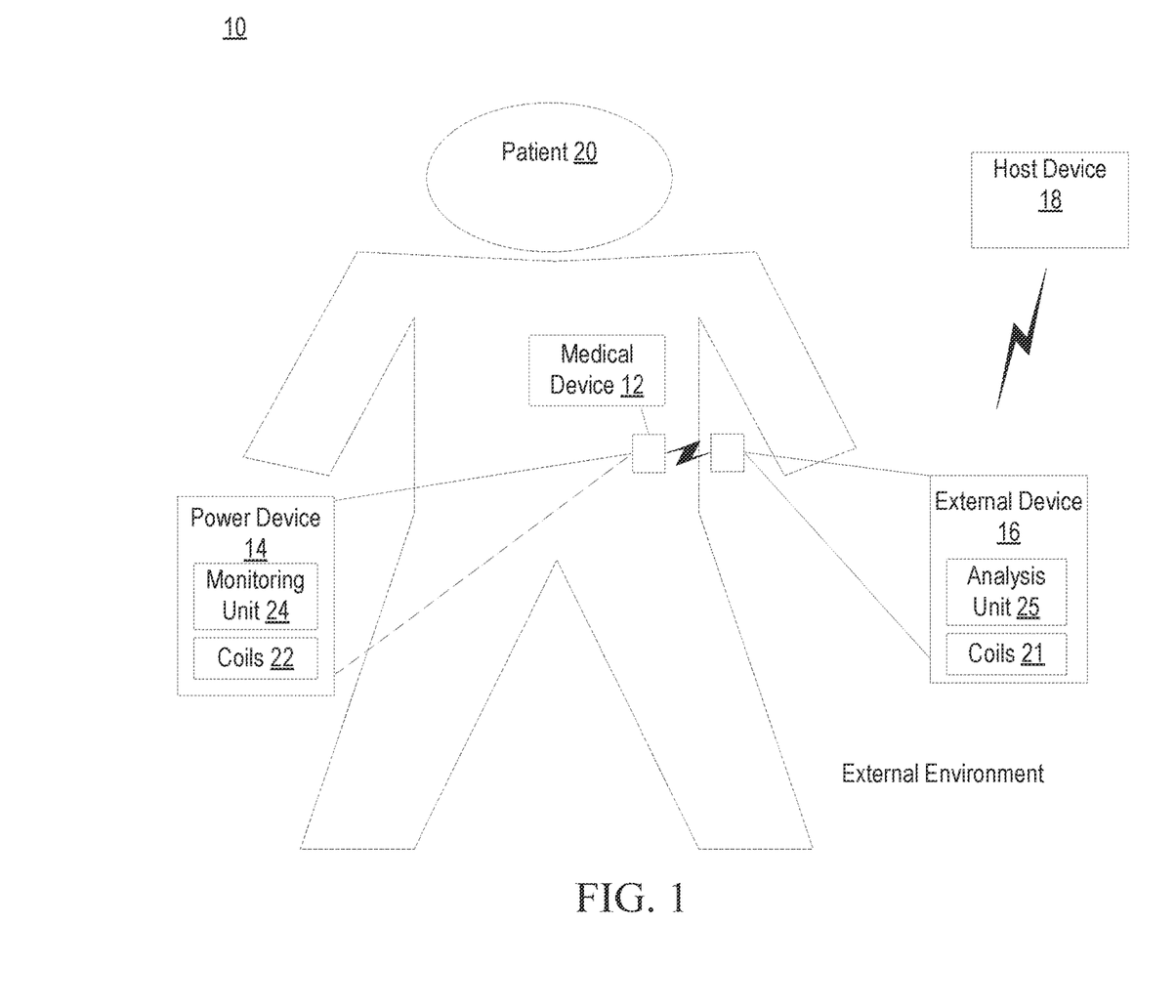
FIG. 1 is a diagram of a system according to principles of the invention.

Referring now to the drawing figures, in which like elements are referred to by like reference numerals, there is shown in FIG. 1 a schematic diagram of a system 10, according to one or more embodiments. System 10 includes one or more medical devices 12 in electrical communication with one or more power devices 14 such as via one or more wired connection, for example. System 10 includes one or more external devices 16 in electrical communication with the power device 14 such as using wireless signals and/or wireless communication. System 10 may optionally include a host device 18 in communication with external device 16.

Medical device 12 may correspond to any medical device that is implantable within a patient 20 and that may use power received from an external power source to perform at least one function. For example, medical device 12 may be a left ventricular assist device (LVAD), other assist devices, devices with rechargeable batteries, among other devices known in the art. Power device 14 includes one or more coils for receiving wireless power signals where the power signals may be electrically converted to power that is usable by medical device 12 as is known in the art. Power device 14 includes monitoring unit 24 that is configured to perform one or more power device 14 functions as described herein such as with respect to detecting a reduction in performance in receiving wireless power signals as described herein.

External device 16 includes coils 21 for providing wireless power signals to power device 14 as is known in the art. In one or more embodiments, external device 16 includes analysis unit 25 that is configured to perform one or more determinations based at least in part on information/data received from power device 14 and/or medical device 12, and other data that that may be determined by external device 16, as described herein. In particular, external device 16 may be in data communication with one or more of power device 14, medical device 12, host device 18, etc., via one or more wireless communication protocols. In one or more embodiments, the wireless power signals communicated between coils 22 and 24 may transfer data between power device 14 and external device 16. Alternatively, the wireless power signals may be used solely for providing power such that these signals do not carry data.

External device 16 and/or power device 14 and/or medical device 12 may be in data communication with host device 18 where host device 18 may be configured to display one or more notifications, communicate with other devices with one or more networks, etc. An example implementation, in accordance with one or more embodiments, of medical device 12, power device 14 and external device 16 discussed in the preceding paragraphs will now be described with reference to FIG. 2. System 10 includes power device 14 that includes hardware 26. The hardware 26 may include a communication interface 28 for setting up and maintaining a wired or wireless connection with an interface of a different communication device of the system 10 such as with one or more of medical device 12, external device 16 and host device 18.

Figure 2:
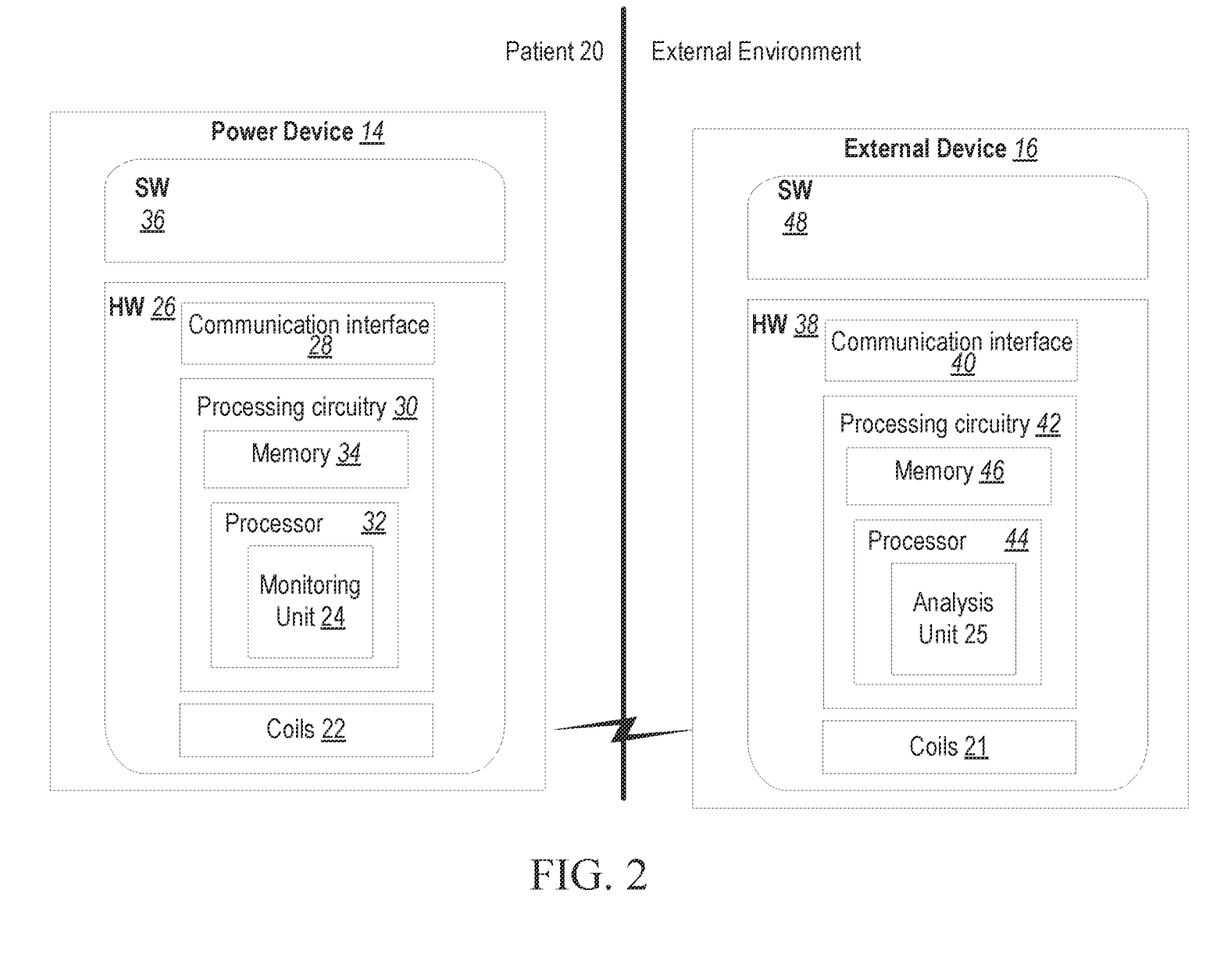
FIG. 2 is a diagram of some devices of the system according to the principles of the invention.

In the embodiment shown, the hardware 26 of the power device 14 further includes processing circuitry 30. The processing circuitry 30 may include a processor 32 and a memory 34. In particular, in addition to or instead of a processor, such as a central processing unit, and memory, the processing circuitry 30 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 32 may be configured to access (e.g., write to and/or read from) the memory 34, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

Thus, the power device further has software 36 stored internally in, for example, memory 34, or stored in external memory (e.g., database, storage array, network storage device, etc.) accessible by the power device 14 via an external connection. The software 36 may be executable by the processing circuitry 30. The processing circuitry 30 may be configured to control any of the methods and/or processes described herein and/or to cause such methods, and/or processes to be performed, e.g., by power device 14. Processor 32 corresponds to one or more processors 32 for performing power device 14 functions described herein. The memory 34 is configured to store data, programmatic software code and/or other information described herein. In some embodiments, the software 36 may include instructions that, when executed by the processor 32 and/or processing circuitry 30, causes the processor 32 and/or processing circuitry 30 to perform the processes described herein with respect to power device 14. For example, processing circuitry 30 of the power device 14 may include monitoring unit 24 configured to perform one or more power device 14 functions as described herein such as with respect to TETS for wireless transfer of power from an external energy transfer coil to an implantable energy transfer coil, as described herein.

System 10 also includes external device 16 that may be configured to be positioned external of patient 20. External device 16 includes hardware 38. The hardware 38 may include a communication interface 40 for setting up and maintaining a wired or wireless connection with an interface of a different communication device of the system 10 such as with one or more of medical device 12, power device 14 and host device 18. For example, communication interface 40 may receive one or more of an indication of at least one determined measurable electrical characteristic, and indication of power received by the power device 14, among other data and/or indications.

In the embodiment shown, the hardware 38 of the external device 16 further includes processing circuitry 42. The processing circuitry 42 may include a processor 44 and a memory 46. In particular, in addition to or instead of a processor, such as a central processing unit, and memory, the processing circuitry 42 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 44 may be configured to access (e.g., write to and/or read from) the memory 46, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

Thus, the external device 16 further has software 48 stored internally in, for example, memory 46, or stored in external memory (e.g., database, storage array, network storage device, etc.) accessible by the external device 16 via an external connection. The software 48 may be executable by the processing circuitry 42. The processing circuitry 42 may be configured to control any of the methods and/or processes described herein and/or to cause such methods, and/or processes to be performed, e.g., by external device 16. Processor 44 corresponds to one or more processors 44 for performing external device 16 functions described herein. The memory 46 is configured to store data, programmatic software code and/or other information described herein. In some embodiments, the software 48 may include instructions that, when executed by the processor 44 and/or processing circuitry 42, causes the processor 44 and/or processing circuitry 42 to perform the processes described herein with respect to power device 14. For example, in one or more embodiments, processing circuitry 42 of the external device 16 may include analysis unit 25 configured to perform one or more external device 16 function such as with respect to analysis of measurement data and/or other data, as described herein. For example, external device 16 may determine one or more of a wireless power transfer efficiency, long term moving average of at least one measurable electrical characteristic, among other determinations, as described herein. In one or more embodiments, analysis unit 25 may be configured to perform similar functions of monitoring unit 24 but with respect to external device 16. For example, analysis unit 25 may perform Blocks S100 and S102, described below, but with respect to a plurality of pathways in the external device 16.

Figure 3:
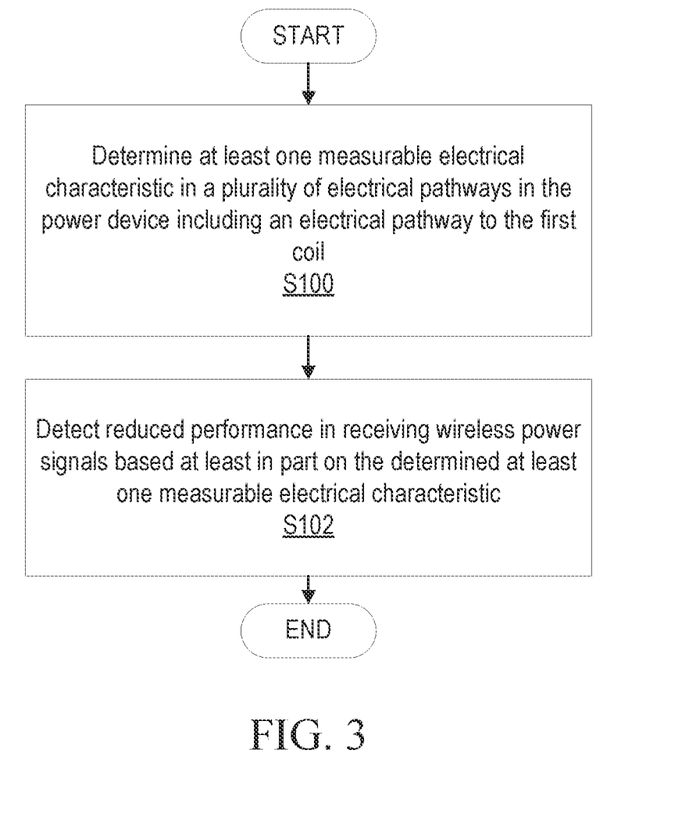
FIG. 3 is a flowchart of a process for detecting/determining reduced performance according to the principles of the invention.

FIG. 3 is a flowchart illustrating an exemplary process of power device 14 according to some embodiments of the present disclosure. One or more Blocks and/or functions performed by power device 14 may be performed by one or more elements of power device 14 such as by monitoring unit 24 in processing circuitry 30, processor 32, etc. In one or more embodiments, power device 14 such as via one or more of processing circuitry 30, processor 32, monitoring unit 24, communication interface 28, etc. is configured to determine (Block S100) at least one measurable electrical characteristic in a plurality of electrical pathways in the power device 14 including an electrical pathway to the first coil, as described herein.

In one or more embodiments, power device 14 such as via one or more of processing circuitry 30, processor 32, monitoring unit 24, communication interface 28, etc. is configured to detect (Block S102) reduced performance in receiving wireless power signals based at least in part on the determined at least one measurable electrical characteristic, as described herein.

Alternatively or in addition to detecting reduced performed in receiving wireless power signals, processing circuitry 30 may detect reduced performance in using the wireless power signals and/or reduced performance in another measurable performance characteristic related to communicating wireless power signals and/or using the wireless power signals to power the medical device 12.

According to one or more embodiments, the plurality of electrical pathways includes a feedthrough cables, connectors and coil windings. According to one or more embodiments, the processing circuitry 30 is further configured to trigger a notification if any one of the at least one measurable electrical characteristic is one of below and above a predefined threshold, or meets a predefined criterion. According to one or more embodiments, the power device 14 is positioned one of proximate and within the medical device 12.

For example, the detection of reduced performance may be based at least on one of periodic/aperiodic monitoring and/or determining of at least one measurable electrical characteristic such as impedance/continuity checks of connections (i.e., at least one impedance value), etc.

Figure 4:
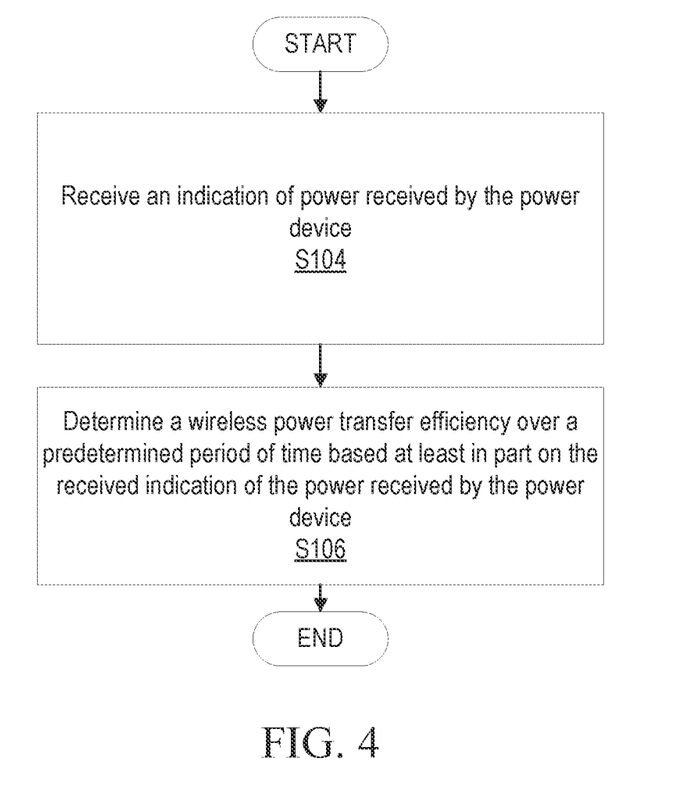
FIG. 4 is a flowchart of a process for analysis according to the principles of the invention.

FIG. 4 is a flowchart illustrating an exemplary process of external device 16 according to some embodiments of the present disclosure. One or more Blocks and/or functions performed by external device 16 may be performed by one or more elements of external device 16 such as by analysis unit 25 in processing circuitry 42, processor 44, etc. In one or more embodiments, external device 16 such as via one or more of processing circuitry 42, processor 44, analysis unit 25, communication interface 40, etc. is configured to receive (Block S104) an indication of power received by the power device 14, as described herein. In one or more embodiments, external device 16 such as via one or more of processing circuitry 42, processor 44, analysis unit 25, communication interface 40, etc. is configured to determine (Block S106) a wireless power transfer efficiency over a predetermined period of time based at least in part on the received indication of the power received by the power device 14, as described herein.

According to one or more embodiments, the wireless power transfer efficiency over the predetermined period of time corresponds to a long term moving average. According to one or more embodiments, the long term moving average indicates whether performance is degrading due to at least one non-alignment factor between the first coil 22 and second coil 21. According to one or more embodiments, the at least one non-alignment factor includes at least one of increased fat thickness of a person in which the implantable power device 14 is implanted and degradation of at least one material characteristic of the implantable power device 14. For example, increased fat thickness of a person may be caused by an increase in fatty tissue or subcutaneous fluid accumulation where the increased fat thickness may result in increased distance between the implanted coil and the skin surface. According to one or more embodiments, the at least one non-alignment factor includes at least one characteristic of a person that causes the distance between the implanted coil and the skin surface (or external coil) to increase. According to one or more embodiments, the processing circuitry 30 is further configured to trigger a notification indicating if the long term moving average meets a predefined threshold.

According to one or more embodiments, the processing circuitry 42 is further configured to receive an indication of the determined at least one measurable electrical characteristic, and determine a long term moving average based at least in part on the determined at least one measurable electrical characteristic. According to one or more embodiments, the processing circuitry 42 is further configured to determine one or more of a quality factor (Q) assessment, power transmitted assessment of power transfer efficiency versus measured temperature, long term efficiency trending (i.e., wireless power transfer efficiency) based at least in part on data and/or indications received from power device 14 and/or medical device 12.

In one or more embodiments, the external device 16 may determine at least one measurable electrical characteristic associated with the external device 16. For example, the at least one measurable electrical characteristic may include at least one characteristic of one or more of coil 21, cable(s) of external device 16, interconnects of external device 16, etc. In one or more embodiments, the at least one measurable electrical characteristic is determined/measured by the external device 16 during one or more predefined/predetermined time periods. For example, one or more measurable electrical characteristics may be measured when there is no wireless power transfer between the power device 14 and external device 16 and/or during times when there is no wireless power being transmitted from the external device 16. In one or more embodiments, the external device 16 may target specific predefined times to perform the measurements and/or may perform periodic measurements when wireless power transfer is not occurring. The measurements may be processed by external device 16 to determine whether to keep the measurements.

In one or more embodiments, the external device 16 may determine that there is no a metal object proximate the external device 16 by at least in part perform and storing measurements when the coil 21 is moving (e.g., the external device 16 may move such as based on sensor data associated with the external device 16 such accelerometer data), which may imply that the external device 16 is not positioned on an object that may be metal.

Long Term Efficiency Trending

While the efficiency of energy transfer over a short time scale (i.e., a time scale below a predefined threshold) can be influenced by the alignment of the external device 16 and the implanted coils 22, a long term average of the efficiency may be used to indicate and/or detect degrading performance. In one or more embodiments, the long term efficiency is determined by external device 16 based at least in part on received data and/or indications from, for example, power device 14. Degrading performance could be a result of increasing fat thickness of patient 20 between internal/implanted coils 22 and external coils 21 or due to gradual worsening of material characteristics such as conductivity. To detect these types of degradation, the system 10 and/or one or more devices in system 10 may periodically measure and store efficiency values of the energy transfer between coils 21 and 22 that may be based at least in part on received power values reported by power device 14. A long-term moving average could be compared with an average value captured near the time of implant of power device 14 and/or medical device 12.

When the long term average crosses a threshold (either expressed as an absolute limit or a delta compared to the baseline), an automatic indication of degraded performance may be presented to the patient or clinician (via a wireless link and/or host device 18). Alternatively, the long term trend of efficiency over time could be presented in a periodic programmer or CareLink report to allow the clinician (or MDT) to make more subjective assessments of degrading performance.

Measurable Electrical Characteristics Such as Periodic Impedance/Continuity Check of Connection Power device 14 (i.e., implanted controller or iController) may periodically measure at least one measurable electrical characteristic such as the impedance and continuity of one or more electrical pathways that traverse through one or more of feedthroughs, connectors, header on power device 14 through connector, cable, coil windings of coils 22. These measurements may be used to detect both sudden loss of continuity below and/or above some threshold value, or the gradual worsening of measured electrical characteristic(s). In one or more embodiments described herein, the sudden loss of continuity may correspond to an increase in impedance by at least a predefined amount and/or impedance exceeding a predefined threshold.

Further, in one or more embodiments, external device 16 such as via analysis unit 25 may be configured to periodically measure at least one measurable electrical characteristic such as the impedance and continuity of one or more electrical pathways that traverse through one or more of feedthroughs, connectors, header on external device 16 through connector, cable, coil windings of coils 21. These measurements may be used to detect both sudden loss of continuity below and/or above some threshold value, or the gradual worsening of measured electrical characteristic(s). In one or more embodiments described herein, the sudden loss of continuity may correspond to an increase in impedance by at least a predefined amount and/or impedance exceeding a predefined threshold.

Q Assessment

Figure 5:
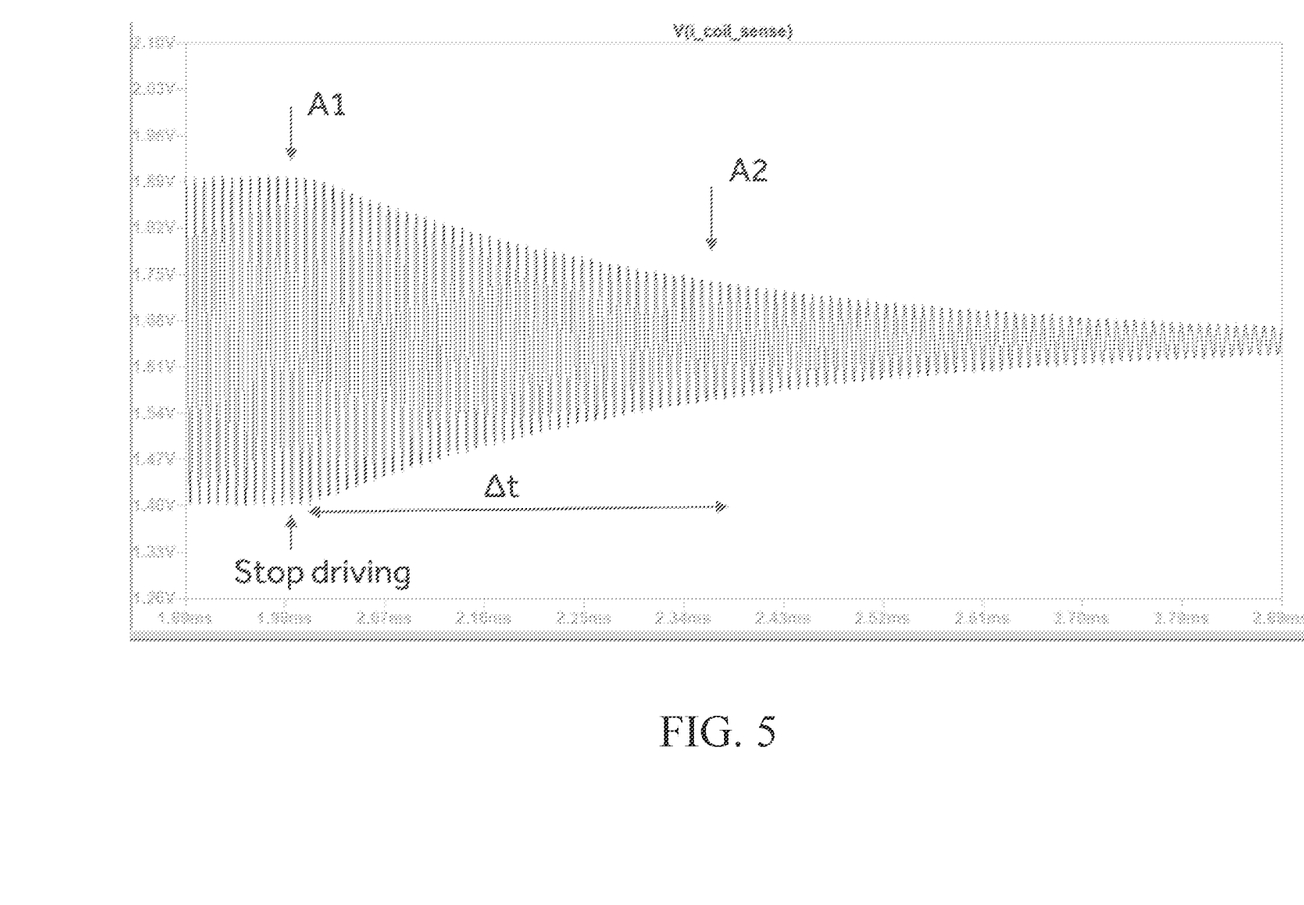
FIG. 5 is a diagram of related to quality factor according to the principles of the invention.
Figure 6:
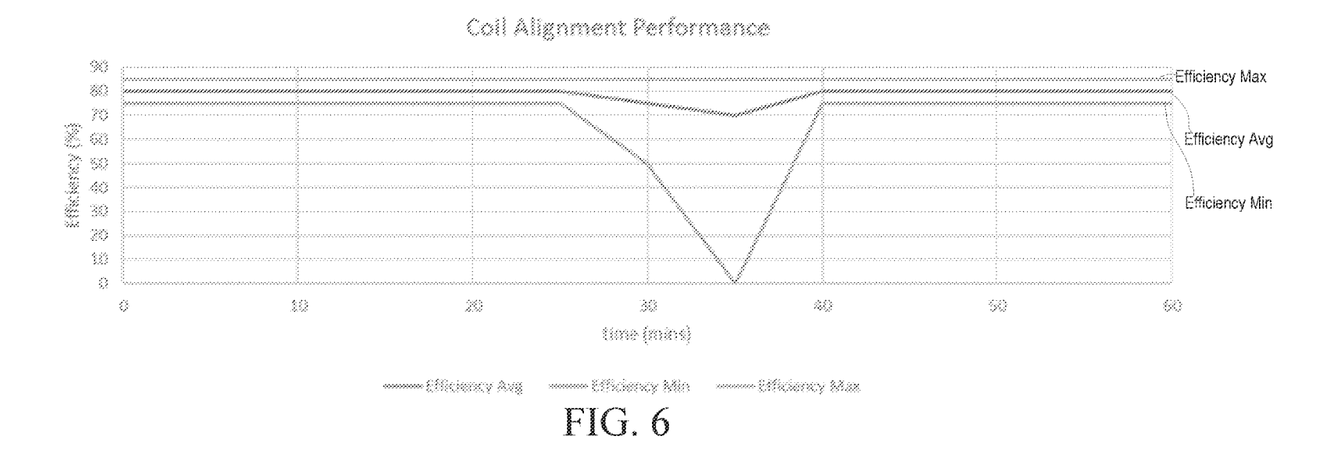
FIG. 6 is a diagram of coil alignment performance according to the principles of the invention.
Figure 7:
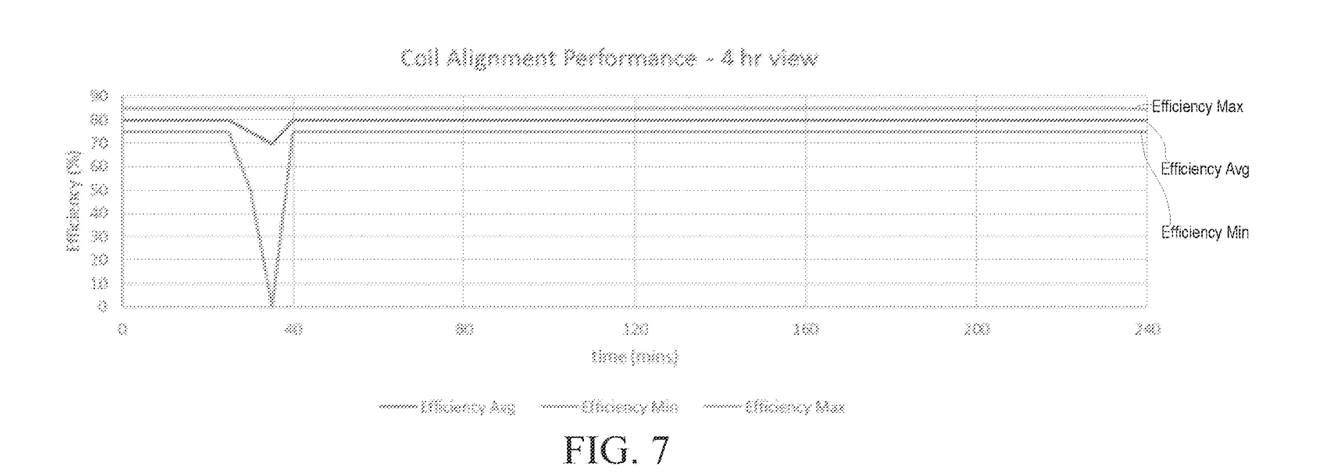
FIG. 7 is a diagram of coil alignment performance for a four-hour view according to the principles of the invention.
Figure 8:
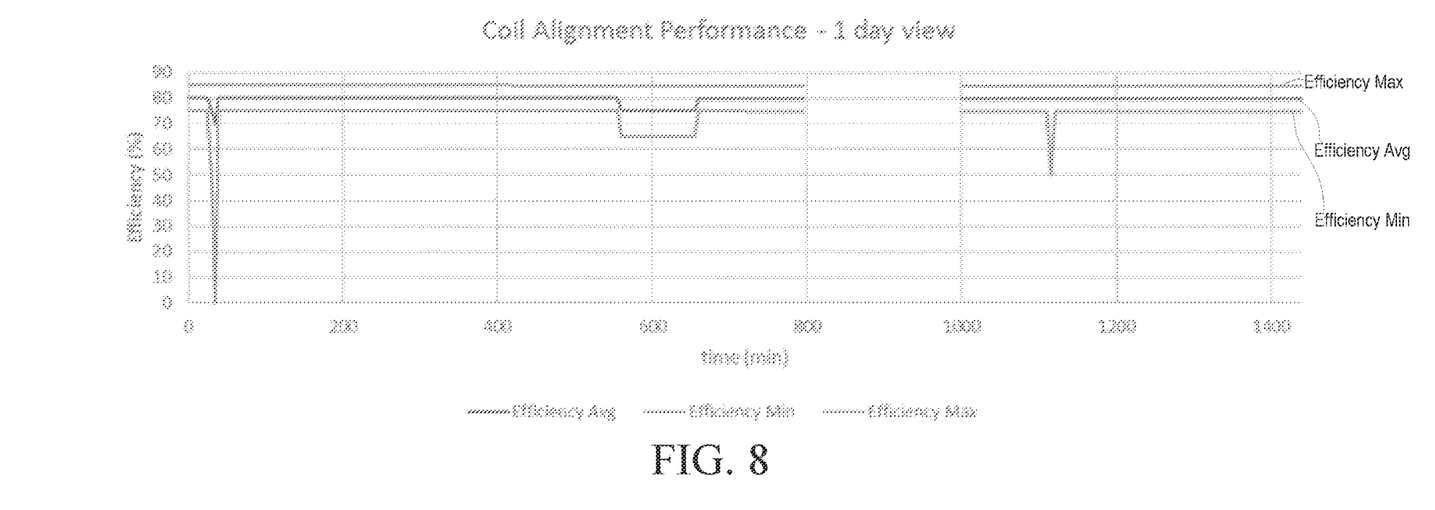
FIG. 8 is a diagram of coil alignment performance for a 1 day view according to the principles of the invention.
Figure 9:
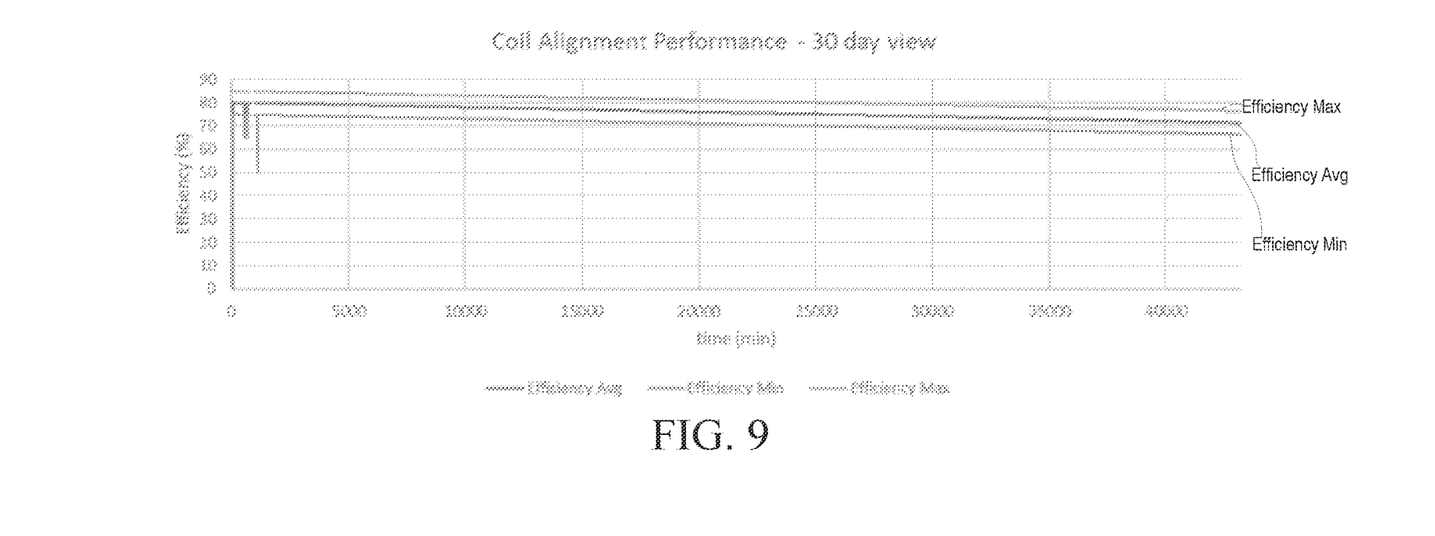
FIG. 9 is a diagram of coil alignment performance for a 30 day view according to the principles of the invention.

A quality factor (Q) of a coil such as external coil 21 may be determined by external device 16 based on the following:

$$Q = 2\prod f\frac{L}{R} \quad \text{decay} := e^{\left(\frac{-2\Pi f_0 \Delta t}{2Q}\right)} = \frac{A_2}{A_1}$$

$$Q(f, \Delta t, \text{decay}) = \frac{-\prod f \Delta t}{\ln(\text{decay})}$$

A1 and A1 are illustrated in FIG. 5. Q may be measured when not charging by stopping the driving of the coil and measuring ringdown, for example. Q that does not follow a normal distribution with finite range may be used to detect failure modes for power device 14 and/or external device 16. In one or more embodiments, Q may be modeled for comparison to measured Q and/or for detecting a failure. In one or more embodiments, Q may be determined by power device 14 with respect to coil 21 as described above.

Power Transmitter (i.e., Power Device 14) Assessment of Power Transfer Efficiency Versus Measured Temperature Instead of, or in addition to, having the power device 14 monitoring the TETS system integrity, the external system (e.g., external device 16, host device 18, etc.) could be used to evaluate performance degradation by monitoring efficiency and component temperature levels. For example, if the efficiency monitored by external device 16 is getting worse but the temperature level(s) of one or more components at power device 14 and/or external device 16 remain the same or within a predefined temperature range, then processing circuitry 42 may determine that the reduced efficiency is not caused by the one or more components of power device 14 or external device 16 and/or is caused by misalignment of the power device 14 with the external device 16. In another example, if the monitored efficiency is getting worse and the temperature level(s) of one or more components are increasing and/or are outside a predefined temperature range, then processing circuitry 42 may determine that the reduced efficiency is caused by the one or more components of power device 14 and/or one or more components of external device 16.

Performance Examples

FIGS. 6-9 are diagrams of coil alignment performance over various time periods in accordance with one or more embodiments of the invention. In particular, the long term alignment tracking provided by monitoring unit 24 and/or analysis unit 25 logs data related to TETS coil alignment. While not shown in FIGS. 6-9, an indicator of historical maximum achieved efficiency (and a timestamp of when that occurred) may be used to allow a longer term comparison of the current and historical efficiency. For example, data logging related to TETS coil alignment performance may occur every 5 minutes where the following data points are logged:

Minimum efficiency over the previous 5 minutes;
Maximum efficiency over the previous 5 minutes; and
Average efficiency over the previous 5 minutes.

The long term alignment trend information may be communicated to host device 18 and/or other device for display to a user. The display may allow for selection of views of various time periods such as 1 hours, 4 hours, 1 day, 3 days, 7 days, 14 days, 30 days similar to other 5-minute log data such as power, speed flow, pulsitility of a device such as medical device 12. If a remote monitoring transmission to CareLink has occurred, the trend is visible on the CareLink Quicklook screen as a view of the last 14 days; however, no data points may be logged while in Free mode (i.e., from the initial press of "intent to enter Free mode" until TETS power is re-established for more than 1 minute, for example). In one or more embodiments, free mode may correspond to a time period where the power device 14 is utilizing implanted battery power rather than TETS power from the external device 16. The log data may be stored temporarily a power device 14 such as via memory 34 until the next connection (e.g., BLUETOOTH connection) with external device 16 (e.g., iController), during which the log data is transmitted to external device 16 for long term storage.

Therefore, including one or more of the features described herein into an implanted LVAD system may provide significant hazard mitigation supporting the safety/efficacy profile of the system, increase patient/clinician confidence in the system 10, among other advantages.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Firmware may correspond to software that is stored in read-only memory. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system, comprising:
   a power device implantable within a patient for powering an implantable medical device, the power device including:
      a first coil configured to receive wireless power signals for powering the implantable medical device; and
      processing circuitry configured to:
         determine at least one measurable electrical characteristic in a plurality of electrical pathways in the power device including an electrical pathway to the first coil; and
         detect reduced performance in receiving wireless power signals based at least in part on the at least one measurable electrical characteristic;
   an external device positioned outside of the patient for providing power to the implantable medical device, the external device including:
      a second coil for transmitting the wireless power signals; and
      processing circuitry configured to:
         receive an indication of power received by the power device; and
         determine a wireless power transfer efficiency over a predetermined period of time based at least in part on the indication of the power received by the power device, wherein the wireless power transfer efficiency over the predetermined period of time corresponds to a long term moving average.

2. The system of claim 1, wherein the long term moving average indicates whether performance is degrading due to at least one non-alignment factor between the first coil and the second coil.

3. The system of claim 2, wherein the at least one non-alignment factor includes at least one of increased fat thickness of a person in which the power device is implanted and degradation of at least one material characteristic of the power device.

4. The system of claim 1, wherein the processing circuitry is further configured to trigger a notification if the long term moving average meets a predefined threshold.

5. The system of claim 1, wherein the processing circuitry is further configured to:
   receive an indication of the at least one measurable electrical characteristic; and
   determine the long term moving average based at least in part on the at least one measurable electrical characteristic.

6. The system of claim 1, wherein the plurality of electrical pathways includes feedthrough cables, connectors and coil windings.

7. The system of claim 1, wherein the processing circuitry is further configured to trigger a notification if any one of the at least one measurable electrical characteristic is below a predefined threshold.

8. The system of claim 1, wherein the power device is positioned at least one of proximate or within the implantable medical device.

9. The system of claim 1, wherein the processing circuitry is further configured to trigger a notification if any one of the at least one measurable electrical characteristic is above a predefined threshold.

10. A method comprising:
   determining at least one measurable electrical characteristic in a plurality of electrical pathways in a power device of a system, wherein the power device is implantable within a patient for powering an implantable medical device, wherein the power device includes a first coil configured to receive wireless power signals for powering the implantable medical device, and wherein the power device includes an electrical pathway of the plurality of electrical pathways to the first coil;
   detecting reduced performance in receiving wireless power signals based at least in part on the at least one measurable electrical characteristic;
   providing, by an external device positioned outside of the patient, power to the implantable medical device, wherein the system includes the external device, and wherein the external device includes a second coil for transmitting the wireless power signals;
   receiving an indication of power received by the power device; and
   determining a wireless power transfer efficiency over a predetermined period of time based at least in part on the indication of the power received by the power device, wherein the wireless power transfer efficiency over the predetermined period of time corresponds to a long term moving average.

11. The method of claim 10, wherein the long term moving average indicates whether performance is degrading due to at least one non-alignment factor between the first coil and the second coil.

12. The method of claim 11, wherein the at least one non-alignment factor includes at least one of increased fat thickness of a person in which the power device is implanted and degradation of at least one material characteristic of the power device.

13. The method of claim 10, further comprising triggering a notification if the long term moving average meets a predefined threshold.

14. The method of claim 10, further comprising:
   receiving an indication of the at least one measurable electrical characteristic; and determining the long term moving average based at least in part on the at least one measurable electrical characteristic.

15. The method of claim 10, wherein the plurality of electrical pathways includes feedthrough cables, connectors and coil windings.

16. The method of claim 10, further comprising triggering a notification if any one of the at least one measurable electrical characteristic is below a predefined threshold.

17. The method of claim 10, wherein the power device is positioned at least one of proximate or within the implantable medical device.

18. The method of claim 10, further comprising triggering a notification if any one of the at least one measurable electrical characteristic is above a predefined threshold.

* * * * *